US00PP21819P2

(12) United States Plant Patent
Kapusta

(10) Patent No.: US PP21,819 P2
(45) Date of Patent: Mar. 29, 2011

(54) ***LONICERA* PLANT NAMED 'INOV42'**
(50) Latin Name: *Lonicera henryi×japonica*
Varietal Denomination: Inov42

(75) Inventor: Véronique Kapusta, Beaucouzé (FR)

(73) Assignees: Institut National de la Recherche Agronomique, Paris (FR), part interest; Saphinov S.N.C., Beaufort (FR), part interest ( * ) Notice: Subject to any disclaimer, the term of this patent is extended or adjusted under 35 U.S.C. 154(b) by 0 days.

(21) Appl. No.: 12/584,236

(22) Filed: Sep. 2, 2009

(51) Int. Cl.
*A01H 5/00* (2006.01)

(52) U.S. Cl. ..... Plt./226
(58) Field of Classification Search ..... Plt./226

See application file for complete search history.

*Primary Examiner*—June Hwu
(74) *Attorney, Agent, or Firm*—Penny J. Aguirre

(57) ABSTRACT

A new cultivar of *Lonicera*, 'Inov42', characterized by its foliage that is persistent, dense and evergreen in winter in France, its dense flowering display of fragrant inflorescences in June that emerge white in color with purple-red markings and turn orange as they mature, its resistance to powdery mildew, black spot, and green fly and its relatively compact vining plant habit.

2 Drawing Sheets

Botanical classification: *Lonicera henryi×japonica.*
Variety denomination: 'Inov42'.

BACKGROUND OF THE INVENTION

The present invention relates to a new and distinct cultivar of *Lonicera,* botanically of hybrid origin, and will be referred to hereafter by its cultivar name, 'Inov42'. 'Inov42' is a new cultivar of honeysuckle, a vine grown for use as an ornamental landscape plant.

The new Invention arose from an ongoing controlled breeding program in Beaucouzé, France. The Inventor made a cross in summer of 1993 between an unnamed plant of *'Lonicera henryi'* as the female parent and *Lonicera japonica* 'Aureoreticulata' (not patented) as the male parent. 'Inov42' was selected from amongst the resulting seedlings as a single unique plant in June 2003.

Asexual reproduction of the new cultivar was first accomplished by the Inventor using softwood stem cuttings in April of 2004 in Beaucouzé, France. The characteristics of this cultivar have been determined to be stable and are reproduced true to type in successive generations.

SUMMARY OF THE INVENTION

The following traits have been repeatedly observed and represent the characteristics of the new cultivar as grown outdoors in a trial plot for five years in Beaucouzé, France. These attributes in combination distinguish 'Inov42' as a unique cultivar of *Lonicera.*

1. 'Inov42' exhibits foliage that is persistent and evergreen in winter in Beaucouzé, France.
2. 'Inov42' exhibits abundant, fragrant flowers in June that emerge white with purple-red markings and turn orange as they mature.
3. 'Inov42' exhibits a relatively compact vining habit of dense foliage.
4. 'Inov42' exhibits resistance to powdery mildew, black spot, and green fly.

'Inov42' is unique as a hybrid between *L. henryi* and *L. japonica* and can be most closely compared to its parent plants. In comparison to the female parent, *L. henryi,* 'Inov42' differs in having more fragrant flowers, a more compact plant habit, leaves that are shorter in length, and foliage that is more persistent throughout the winter. In comparison to the male parent, *L. japonica* 'Aureoreticulata', 'Inov42' differs in having green persistent foliage, whereas the foliage of 'Aureoreticulata' is green with yellow veining and semi-persistent. 'Inov42' also exhibits a more compact plant habit and in having flowers with purple-red markings whereas 'Aureoreticulata' has flowers that lack purple-red markings. Although there are no cultivars of the same hybrid background known to the Inventor, 'Inov42' can be compared to plants from the same breeding program that were also selected for their compact habits and disease resistance. 'Inov71' (U.S. patent application Ser. No. 12/584,237) differs from 'Inov42' in having a more columnar habit and in having flowers that mature to a creamy yellow color rather than orange. 'Inov86' (U.S. patent application Ser. No. 12/584,231) differs from 'Inov42' in having larger flowers that open from dark purple buds and turn dark pink and white and mature to creamy yellow-orange.

BRIEF DESCRIPTION OF THE DRAWING

The accompanying colored photographs were taken in mid summer and illustrate the overall appearance and distinct characteristics of 5 year-old plants the new *Lonicera* as grown in a trial garden in Beaucouzé, France. The photograph in FIG. 1 provides an overall view of the dense, compact habit of 'Inov42' in bloom. The photograph in FIG. 2 provides a close-up view of the foliage of 'Inov42'. The photograph in FIG. 3 provides a close-up view of the inflorescences of 'Inov42'. The colors in the photographs may differ slightly from the color values cited in the detailed botanical description, which accurately describe the colors of the new *Lonicera.*

DETAILED BOTANICAL DESCRIPTION

Figure 1:
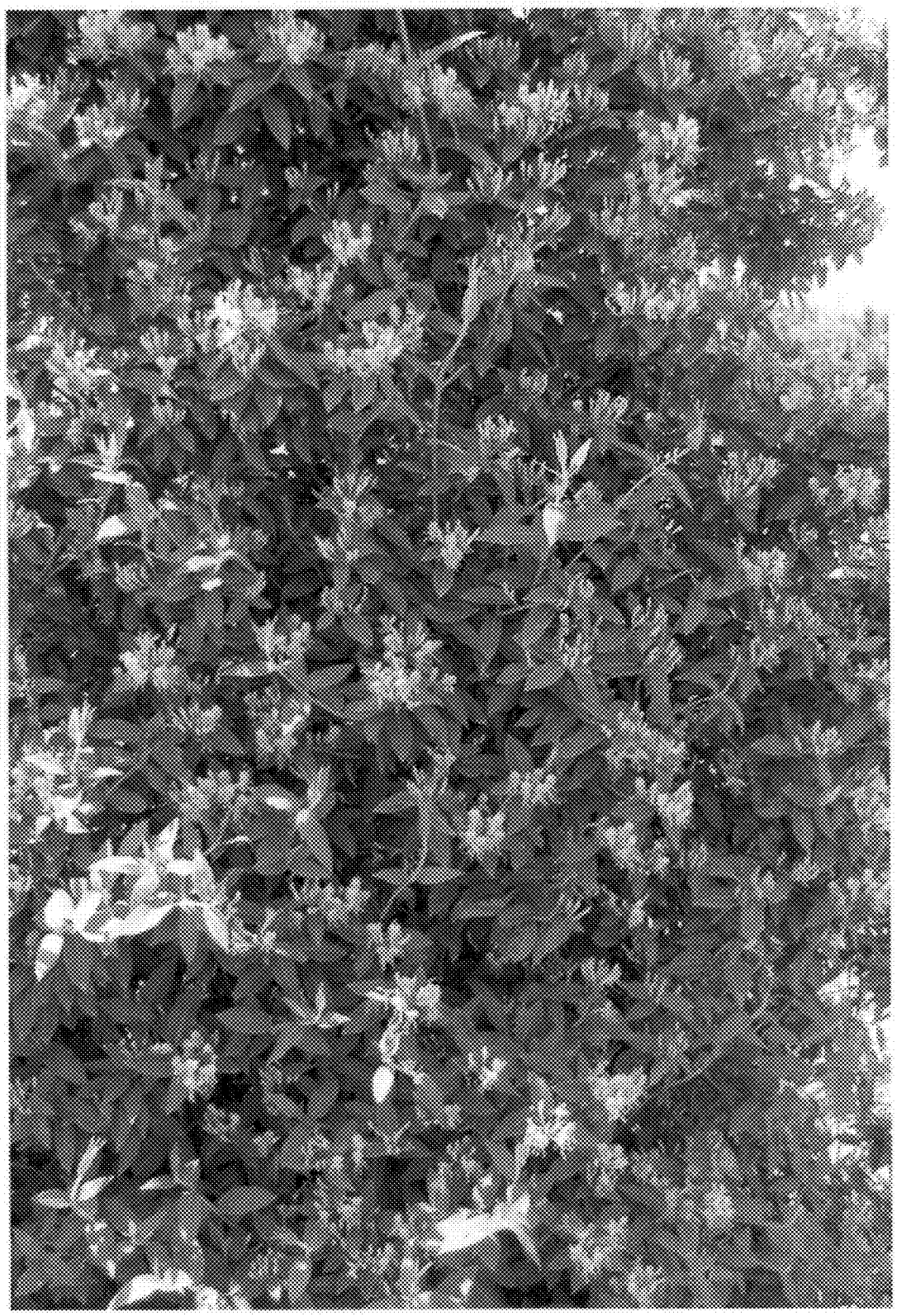
Figure 2:
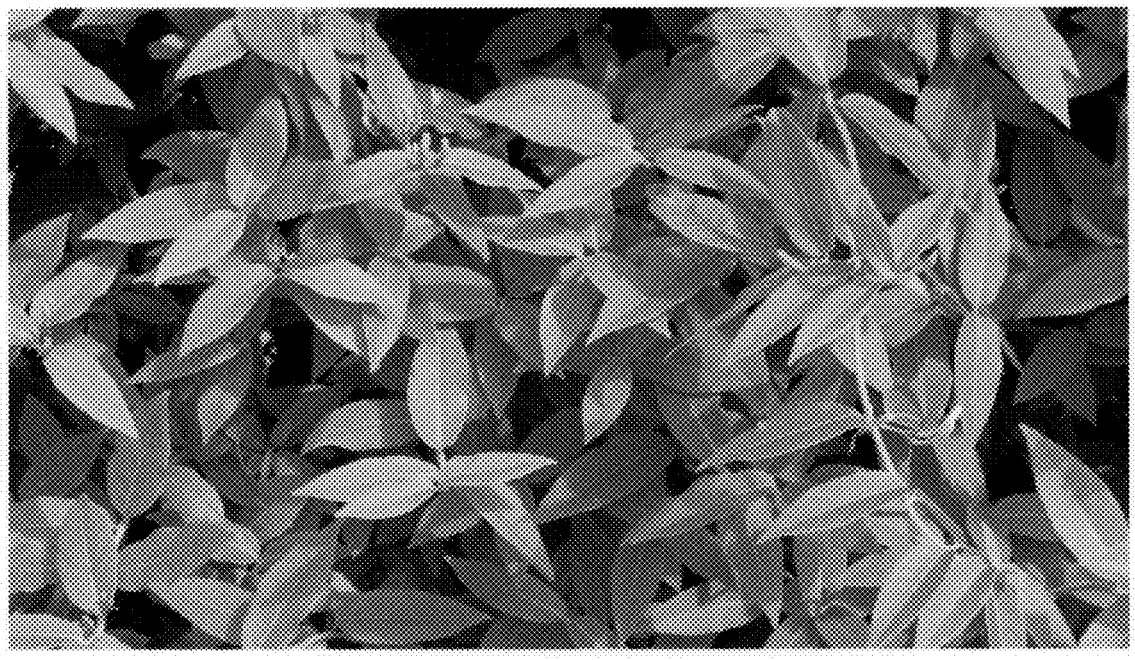
Figure 3:
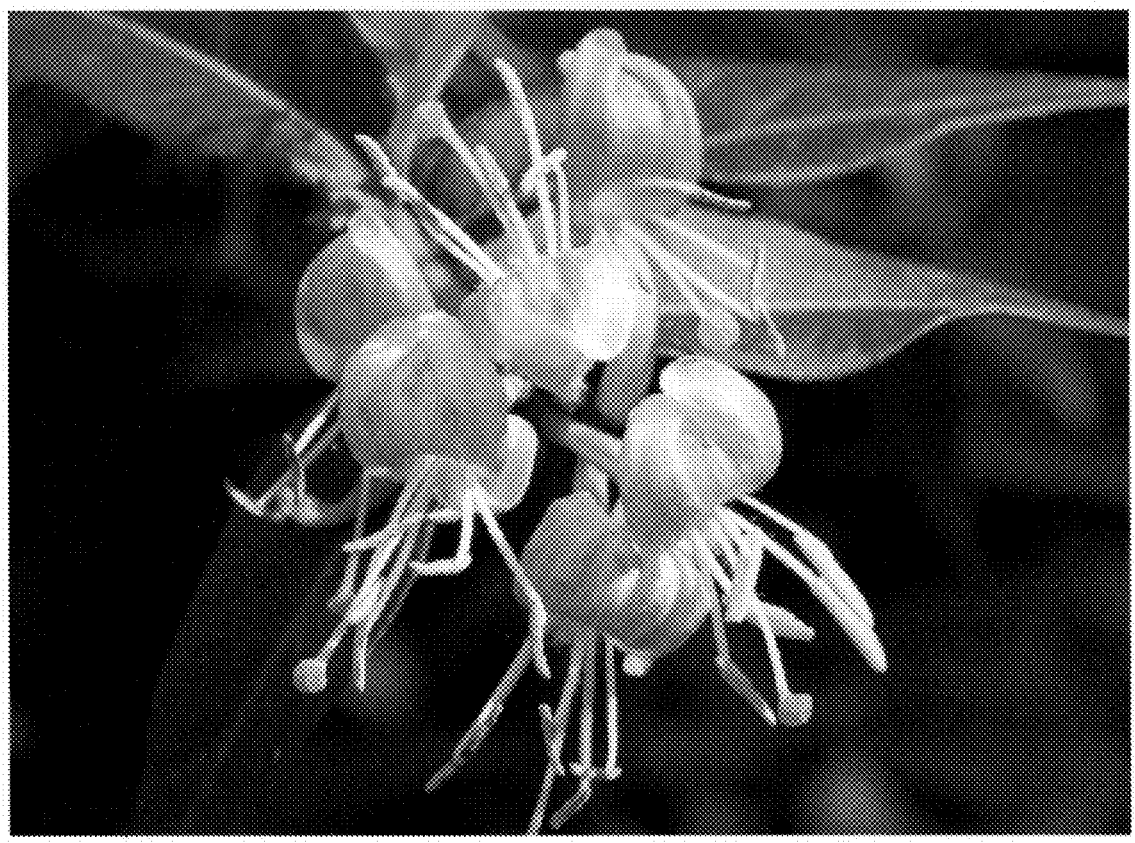

The following is a detailed description of 5 year-old plants the new *Lonicera* as grown in a trial garden in Beaucouzé, France. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period.*—Blooms heavily for about 4 to 5 weeks in June in Beaucouzé, France.

*Plant habit.*—Compact twining vine, persistent, evergreen foliage in winter in Beaucouzé, France.

*Length.*—Reaches 25 to 3 m in length.

*Diseases and pests.*—Has shown good resistance to powdery mildew, black spot, and green fly.

*Hardiness.*—U.S.D.A. Zones 4 to 8.

*Root description.*—Fibrous.

Growth and propagation:

*Propagation.*—Terminal, softwood stem cuttings.

*Growth rate.*—Vigorous.

Stem description:

*Shape.*—Oval.

*Stem color.*—New growth; 145C with some markings of 64C, mature wood; 174A, maturing to bark about 177A.

*Stem size.*—Old wood; ranges about 2.5 cm in diameter near base to 4 mm in diameter on lateral branches, new growth; average of 2 mm in diameter, up to 3 m in length.

*Stem surface.*—New growth; Glabrous and slightly glaucous, mature wood is dull and smooth and becoming bark-like as it ages.

*Internode length.*—An average of 2.5 cm.

*Branching.*—Well branched with new growth emerging in opposite arrangement from axillary nodes.

Foliage description:

*Leaf shape.*—Elliptic.

*Leaf division.*—Simple.

*Leaf base.*—Cuneate.

*Leaf apex.*—Acuminate to cuspidate.

*Leaf fragrance.*—None.

*Leaf venation.*—Pinnate, somewhat conspicuous but not prominent, color on upper surface, 143D, color on lower surface; 144C.

*Leaf margins.*—Entire and pubescent.

*Leaf arrangement.*—Opposite.

*Leaf attachment.*—Petiolate.

*Leaf surface.*—Glabrous on upper surface and lower surface.

*Leaf internode length.*—Ranges from 25 cm.

*Leaf size.*—Ranges from 4 to 6 cm in length and 2 to 2.5 cm in width.

*Leaf quantity.*—Average of 14 pair per branch 30 cm in length.

*Leaf color.*—Newly expanded leaves upper surface; ranges from 144B to 144C, newly expanded leaves lower surface; ranges from 144C to 144D 138A, mature leaves upper surface; ranges from 137B to 137C, mature leaves lower surface; 143C.

*Petioles.*—About 5 mm in length and 2 mm in width, 144C in color, glabrous surface.

*Stipules.*—None.

Inflorescence description:

*Inflorescence type.*—Comprised whorls of tubular flowers at terminus of new growth, 12 flowers per terminal whorl.

*Inflorescence size.*—An average of 6 cm in length and diameter.

*Flower buds.*—Oblanceolate in shape, 158B in color with longitudinal stripes of 72C and 72D and base 64C, an average of 3 cm in length and 5 mm in width (near apex).

*Flower fragrance.*—Fragrant, more than parent plants.

*Lastingness of inflorescence.*—Inflorescence blooms for 2 to 3 weeks with individual flowers lasting about 4 days, lower whorls begin opening first, self-cleaning.

*Flower quantity.*—Average of 12 flowers per terminal inflorescence.

*Flower type.*—Tubular, 2-lipped.

*Flower size.*—Average of 1.5 cm in diameter and 2.8 to 3.2 in depth.

*Peduncles.*—Average of 5.5 mm in length to base of inflorescence and 2 mm in diameter, 145C in color, glaucous surface, oval in shape.

*Bracts.*—2, at base of each whorl, held horizontal, broadly elliptic in shape, 137B in color, glaucous surface, cuspidate apex, truncate base, about 1 cm in width at base and 1.5 cm in length.

*Pedicels.*—None, sessile to peduncle.

*Calyx.*—5-starred, inconspicuous, 1.5 mm in diameter and 0.5 mm in depth.

*Sepals.*—5, un-fused portion in triangular shape, acute apex, fused base, 137C in color, entire margin on tips, glabrous surface.

*Petals.*—5, 4 fused into tube with apex of each free, tube portion is about 1.5 cm in length, 5 mm in width near apex, and 17D in color with shadings of 58C on inner and outer surface, free portion is 2-lipped with upper lip comprised of 4 petals flared outward to reflexed and lower lip comprised of 1 petal that is reflexed, free portion of fused petals are about 2 cm in length and in width together free portion of upper lip petals are triangular in shape and about 4 mm in length and width, free portion of lower lip petal is oblong in shape about 7 mm in length and 4 mm in width, all free petals portions have a rounded apex and entire margin, outer and inner surface is glabrous, color of inner and outer surface is 158B and 158C with shadings and longitudinal stripes of 72C, color of inner and outer surface fades to 20A suffused with 46B.

Reproductive organs:

*Gynoecium.*—1 pistil, about 3.5 cm in length with about 9 mm exserted beyond corolla, style is about 3.2 cm in length, and NN155C in color, stigma is about 2 mm in diameter and 0.7 mm in depth, flattened globose in shape and 145C in color, ovary is inferior, ovoid in shape, about 3 mm in length and 2 mm in diameter and ranges from 143B to 143C in color.

*Androcoecium.*—5 stamens, about 3 cm in length with an average of 7 mm exserted beyond corolla, filaments are NN155C in color, about 2.8 cm in length, anthers are about 4 mm in length, dorsifixed, 11B in color when emerging, pollen is abundant in quantity and 158C in color.

*Fruit and seed.*—True berry, round in shape, about 4.5 mm in diameter, produced in late summer, 103A in color.

It is claimed:

1. A new and distinct cultivar of *Lonicera* plant named 'Inov42' as herein illustrated and described.

* * * * *